US008404630B2

(12) United States Patent
Gambogi et al.

(10) Patent No.: US 8,404,630 B2

(45) Date of Patent: Mar. 26, 2013

(54) FRAGRANCE COMPOSITIONS THAT REDUCE OR ELIMINATE MALODOR, RELATED METHODS AND RELATED CLEANING COMPOSITIONS

(75) Inventors: Joan E. Gambogi, Hillsborough, NJ (US); Mary C. Brauchli, Maplewood, NJ (US); Gary J. Marr, Princeton Junction, NJ (US); Robert C. Vermeer, Columbus, NJ (US)

(73) Assignee: Colgate-Palmolive Company, New York, NY (US)

( * ) Notice: Subject to any disclaimer, the term of this patent is extended or adjusted under 35 U.S.C. 154(b) by 175 days.

(21) Appl. No.: 12/553,165

(22) Filed: Sep. 3, 2009

(65) Prior Publication Data

US 2009/0325855 A1 Dec. 31, 2009

Related U.S. Application Data

(62) Division of application No. 11/353,661, filed on Feb. 14, 2006, now abandoned.

(60) Provisional application No. 60/653,004, filed on Feb. 15, 2005.

(51) Int. Cl.
*A61K 8/18* (2006.01)

(52) U.S. Cl. .......................................................... 512/7

(58) Field of Classification Search ....................... 512/1
See application file for complete search history.

(56) References Cited

U.S. PATENT DOCUMENTS

| | | | | |
|---|---|---|---|---|
| 2,503,280 | A | 4/1950 | Lockwood | |
| 2,507,088 | A | 5/1950 | Bradley | |
| 3,260,744 | A | 7/1966 | Kenkichi et al. | |
| 3,372,188 | A | 3/1968 | Alston et al. | |
| 5,861,146 | A | 1/1999 | Peterson et al. | |
| 5,874,073 | A | 2/1999 | Kaiser et al. | |
| 5,874,394 | A | 2/1999 | Thomas et al. | |
| 6,008,180 | A | 12/1999 | Drapier et al. | |
| 6,127,328 | A * | 10/2000 | D'Ambrogio et al. | 510/237 |
| 6,403,075 | B1 | 6/2002 | Costa | |
| 6,455,086 | B1 * | 9/2002 | Trinh et al. | 426/321 |
| 6,492,314 | B1 | 12/2002 | Jakubicki et al. | |
| 6,506,719 | B1 | 1/2003 | Arvanitidon et al. | |
| 6,610,648 | B2 | 8/2003 | McGee et al. | |
| 6,723,687 | B2 | 4/2004 | Clare | |
| 2003/0092594 | A1 | 5/2003 | Ahmed | |
| 2003/0166499 | A1 | 9/2003 | Yang et al. | |
| 2004/0018950 | A1 | 1/2004 | Foley et al. | |
| 2004/0033926 | A1 | 2/2004 | Szewczyk et al. | |
| 2004/0037799 | A1 | 2/2004 | Costa et al. | |
| 2004/0101504 | A1 | 5/2004 | Kinscherf et al. | |
| 2006/0189503 | A1 | 8/2006 | Gambogi et al. | |

FOREIGN PATENT DOCUMENTS

| | | |
|---|---|---|
| CA | 2437728 | 8/2002 |
| DE | 735096 | 5/1943 |
| EP | 1 203 577 | 5/2002 |
| EP | 1 388 585 | 2/2004 |
| GB | 2 311 296 | 9/1997 |
| NZ | 240754 | 5/1995 |
| NZ | 240753 | 6/1995 |
| WO | WO 95/20027 | 7/1995 |
| WO | WO 97/35947 | 10/1997 |
| WO | 00/37117 | 6/2000 |
| WO | WO 00/61710 | 10/2000 |
| WO | WO 01/79404 | 10/2001 |
| WO | WO 01/96509 | 12/2001 |
| WO | 02/06437 | 1/2002 |
| WO | WO 2004/056957 | 7/2004 |

OTHER PUBLICATIONS

File History from U.S. Appl. No. 11/353,661 as of Sep. 30, 2010.
File History from EP06735043 as of Dec. 18, 2009.
File History from U.S. Appl. No. 12/024,200, filed Feb. 1, 2008.
International Search Report and Written Opinion in International Application No. PCT/US06/005190 mailed Jul. 18, 2006.

* cited by examiner

*Primary Examiner* — Ling Choi
*Assistant Examiner* — Catherine S Branch
(74) *Attorney, Agent, or Firm* — Michael F. Morgan

(57) ABSTRACT

A fragrance composition for control of kitchen malodor, kitchen cleaning and deodorizing products comprising them, and methods for the reduction of malodor utilizing them, the fragrance composition comprising a decyl aldehyde; an allyl amyl glycolate; cis-3-hexenyl acetate; a rose oxide; a terpinolene; and 2,4-dimethyl-3-cyclohexene-1-carbaldehyde.

20 Claims, No Drawings

FRAGRANCE COMPOSITIONS THAT REDUCE OR ELIMINATE MALODOR, RELATED METHODS AND RELATED CLEANING COMPOSITIONS

CROSS-REFERENCE TO RELATED APPLICATIONS

This application is a divisional application of Ser. No. 11/353,661, filed on Feb. 14, 2006, which claims priority, to U.S. provisional patent application Ser. No. 60/653,004, filed Feb. 15, 2005, the contents of each are incorporated herein by reference.

BACKGROUND OF THE INVENTION

Those who cook or work in the kitchen often comment on the disagreeable odors of food and cooking grease that linger after the preparation and/or consumption of a meal, particular those meals that include fish, onions, garlic, leeks, or shellfish. Prior approaches to addressing this problem have included the use in dishwashing products of fragrances that develop blooming or intense odors. Such odors may serve to overpower the targeted malodor and therefore reduce the perception by the user of the malodor. For example, the prior art describes a number of so-called blooming ingredients and compositions able to provide a pleasant fragrance in an area surrounding the dishwashing machine during and after use.

Often these prior art products have an overpowering fragrance that itself may linger too long, in the kitchen. Therefore it is desirable to provide a more subtlety fragranced dishwashing detergent or liquid while still giving good control of kitchen odors. Preferably, such compositions are adapted for use in all types of cleaning products, including those used for manual dishwashing and those used for machine dishwashing.

BRIEF SUMMARY OF THE INVENTION

The invention includes a fragrance composition that contains at least four compounds selected from a decyl aldehydes, an allyl amyl glycolate, cis-3-hexenyl acetate, a rose oxide, a terpinolene, and 2,4-dimethyl-3-cyclohexene-1-carbaldehyde.

The invention also includes a cleaning product that incorporates a surfactant and a fragrance composition comprising: a decyl aldehydes, allyl amyl glycolate, cis-3-hexenyl acetate, rose oxide, terpinolene, and 2,4-dimethyl-3-cyclohexene-1-carbaldehyde.

Methods of reducing and/or eliminating kitchen malodor using these compositions and products are also provided.

DETAILED DESCRIPTION OF THE INVENTION

Described is an invention that includes fragrance and cleaning compositions that reduce or eliminate the perception of the presence of food malodors present in areas where food is prepared, stored, consumed and/or which adhere to the implements used in food preparation and the associated washing up processes. Such food malodors include those caused by vegetables of the Family *Alliaceae* (e.g., garlics, chives, shallots, leeks, garden onion), cruciferous vegetables (broccoli, cauliflower), fish/seafood, cooked food, burned food, cooked oil, burned oil, cooking spices or herbs, overripe or spoiled vegetable matter, or grease. The compositions may be incorporated into cleaning products for use in the kitchen, dining rooms, or other spaces, sink and counter surfaces used in dishwashing or cleaning of food preparation areas, and porous or non-porous surfaces, including dishware and cooking, implements, especially liquid dishwashing products, automatic dishwashing products, cleaning wipes, hard surface cleaners, trash cans, trash can liners and bags, cleaning implements (brooms, sponges, brushes, cloths, etc.). The fragrance compositions may also be included in materials that can be used to fabricate or coat article or surfaces that are used in food preparation or disposal, included paints, varnishes, polymer coatings, plastics, etc. Also included in the invention are cleaning compositions incorporating the methods of reducing malodor by application or agitation in water of the fragrance composition of the invention.

Malodor-reducing fragrance compositions that may be used in a kitchen cleaning product according to this invention are made, for example, by combining at least four of the components: (i) decyl aldehyde (n-decanal), (ii) allyl amyl glycolate, (iii) cis-3-hexenyl acetate, (iv) a rose oxide, (v) terpinolene, and (vi) 2,4-dimethyl-3-cyclohexene-1-carbaldehyde. Preferably at least five or all of the components are combined.

The components of the invention may be obtained from any source known or to be developed in the art. They may be prepared synthetically or they may be extracted from natural sources. For example, n-decanal or allyl amyl glycolate may be obtained from lemon grass, citronella, other plants of the Genus *Cymbopogon* or oil of citrus peels. The rose oxide used in the composition of the invention may be any known or to be developed in the art, and may include combinations of rose oxides. Suitable rose oxides may include (4R,2S)-(−)-cis-rose oxide, (4R,2S)-(+)-cis-rose oxide, (4R,2S)-(+)-trans-rose oxide, (4R,2S)-(−)-trans-rose oxide or combinations of these.

The components of the invention may be in any substituted, unsubstituted in whole or in part and may be any isomers, enantiomers, or racemers of the listed compounds.

When these malodor reducing components are incorporated into a kitchen product, they are suitably present in an amount sufficient to ensure that the product, e.g., a kitchen cleaning product, for example a dishwashing liquid, counteracts kitchen malodors and the smells of residual foods to the desired level of efficiency.

The component present in the fragrance composition of the invention may be present in any amount and/or relative proportion; such amounts and proportions may vary depending on the end use for which product containing the fragrance compositor is intended. However, it may be preferred that the decyl aldehyde and/or allyl amyl glycolate are independently present in an amount of about 0.1 to about 8% by weight, more preferably about 0.5 to about 5%, or 0.3 to about 3% by weight of the composition.

It may be preferred that the cis-3-hexenyl acetate is present in an amount of up to about 5% by weight, preferably about 0.1% to about 3% by weight, more preferably up to about 1.5% by weight of the composition.

It may be preferred that the rose oxide(s) is present in an amount of up to about 2% by weight, preferably about up to 1% by weight, more preferably about 0.1% by weight to about 3% by weight of the composition.

It may be preferred that the terpinolene is present in the composition in an amount up to about 10% by weight, preferably about up to about 0.05% by weight to about 7% by weight of the composition.

It may be preferred that the 2,4-dimethyl-3-cyclohexene-1-carbaldehyde is present in the composition in an amount up to about 3% by weight, preferably about up to about 0.05% to about 2% by weight of the composition.

In some embodiments, it may be preferable that the components of the fragrance composition are present in relative weight proportions as shown in Table I and/or Table II:

TABLE I

| Component | Proportion |
|---|---|
| Decyl aldehydes | About 2.5 |
| Ally amyl glycolate | About 1 |
| Cis-3-hexenyl acetate | About 1 |
| Rose oxide | About 0.5 |
| Terpinolene | About 2 |
| 2.4-dimethyll-3-cyclohexene-1-carbaldehyde | About 3 |

TABLE II

| Component | Proportion |
|---|---|
| Decyl aldehydes | About 0.5 |
| Ally amyl glycolate | About 1.5 |
| Cis-3-hexenyl acetate | About 0.1 |
| Rose oxide | About 0.1 |
| Terpinolene | About 1 |
| 2.4-dimethyll-3-cyclohexene-1-carbaldehyde | About 0.5 |

The fragrance compositions of the invention may contain additional ingredients as well, including additional fragrance compounds, excipients, carriers, or colorants. For example, the fragrance composition may include (a) esters of salicylic acid such as hexyl salicylate, hexenyl salicylate, isoamyl salicylate, benzyl salicylate and cyclohexyl salicylate;

(b) esters of cinnamic acid such as amyl cinnamate, cinnamyl cinnamate and methyl cinnamate;

(c) perfume esters such as allyl cyclohexane propionate, amyl benzoate, para-tertiarybutylcyclohexyl acetate, cedryl acetate, cedryl formate, dihydro-isojasmonate, ethylene brassylate, ethyl undecylenate, geranyl anthranilate, geranyl phenyl acetate, linalyl benzoate, benzyl acetate, linalyl acetate, vetiveryl acetate, terpinyl acetate; especially acetates of $C_{6-12}$ alcohols, for example terpinyl acetate, isononyl acetate, hexyl acetate, 2-tert-butyl-cyclohexyl acetate, p-tert-butyl-cyclohexyl acetate;

(d) aldehydes such as cyclamen aldehyde, lilial, benzaldehyde, citronellal, hydroxy-citronellal;

(e) alcohols such as geraniol, linalool, nerol, phenyl ethyl alcohol, alpha terpineol, eugenol, isoeugenol, alpha-citronellol, dihydromyrcenol, aurantiol, cedrol, phenyl heptanol, phenol hexanol, alpha-santalol, undecavertol (4-methyl-3-decen-5-ol), benzyl alcohol; especially $C_{10}$ unsaturated alcohol e.g., dihydromyrcenol and linalool;

(f) ketones such as benzophenone, dodecalactone, gamma-n-methyl ionone, delta-undecalactone, gamma-undecalactone, laevo-carvone, beta-methylnaphthyl ketone;

(g) nitromusk such as musk ketone, musk tibetine, musk indanone;

(h) terpenes such as orange terpenes, limonene; and (i) nitriles such as citronellyl nitrile.

In one embodiment, additional ingredients are orange terpenes; acetates of alcohols having 6 to 12 carbon atoms, e.g., terpinyl acetate, isononyl acetate, hexyl acetate, 2-tert-butylcyclohexyl acetate, and p-tert-butyl-cyclohexyl acetate; unsaturated alcohols having ten carbon atoms, e.g., dihydromyrcenol and linalool; and citronellyl nitrile.

However, in some embodiments it may be preferred that the fragrance compositions of the invention contains minimal or reduced amounts of one or more of the following compounds: amyl cinnamic aldehyde, 1,3,4,6,7,8-hexahydro-4,6,6,7,8,8-hexamethylcyclopenta-g-2-benzopyran (HHCB), or 1-(1,2,3,4,5,6,7,8-Octahydro-2,3,8,8-tetramethyl-2-naphthalenyl)ethanone. For example, in may be preferred that the composition contains independently:

amyl cinnamic aldehyde in an amount of less than about 15%, more preferably less than about 5% by weight, more preferably less than about 1% by weight of the total fragrance composition;

HHCB in an amount of less than about 20%, more preferably less than about 5% by weight, more preferably less than about 1% by weight of the total fragrance composition;

1-(1,2,3,4,5,6,7,8-Octahydro-2,3,8,8-tetramethyl-2-naphthalenyl)ethanone in an amount of less than about 5%, more preferably less than about 2% by weight, more preferably less than about 0.5% by weight of the total fragrance composition.

In some embodiments it may be preferred that the fragrance composition is substantially free of one or more of these ingredients, or that the ratio of the fragrance composition components (i) to (iv) listed above to one or more of the compounds listed above is about 10 to 1.

The fragrance composition of the invention may be incorporated into a cleaning product. Such cleaning product may take any form; it may be, for example, a dishwashing detergent (liquid, powder, gel, paste; manual or automatic), an all-purpose surface cleaners, and a wipe or pre-treated textile, sponge, broom, or other cleaning implements, detergents for cleaning pots and pans, hand soaps, laundry products and shampoos or other hair care products.

Such products may contain the fragrance composition of the invention in any amount. However, it may be preferable that the fragrance composition is present in an amount of about 2 to about 50% by weight, more particularly about 4 to about 20% by weight, or about 3.5 to about 10% by weight and up to about 9.5% by weight.

In one embodiment, it is preferred that the cleaning product contains one or more surfactants. Any surfactant or mixture of surfactants may be used; types and mixture will vary depending on the intended use of the end product. For example, if the end product is a manual dish detergent, the product may contain one or more ionic and/or non-ionic surfactants. Alternatively, the product may contain one or more surfactants selected from cationic surfactants, linear alkyl benzene sulfonate salts (preferably having 8 to 18 carbon atoms), sulfated alcohol ethoxylates, amine oxide surfactants and/or amphoteric surfactants.

An embodiment that is a manual dishwashing liquid could include (i) at least two surfactants selected from cationic surfactants (e.g, quaternary ammonium surfactants, dialkyl dimethyl ammonium chloride), nonionic surfactants (alkylpolyglucosides or polyoxyethylenated alcohols), linear alkyl benzene sulfonate salts (e.g., sodium and/or magnesium salts), sulfated alcohol ethoxylates ($C_8$-$C_{18}$ ethoxylated alkyl ether sulfate; the sodium salt and/or the ammonium salt), amine oxide surfactants (a $C_{12}$/$C_{14}$alkyl amido propyl dimethyl amine oxide), amphoteric surfactants (a trialkyl glycine surfactant, for example cocobetaine).

In another embodiment, the invention includes cleaning products that are liquid dishwashing liquids of conventional formulations but which contain the fragrance composition of the invention. The formulations for a dishwashing liquid in accordance with the invention may, for example, be as described in U.S. Pat. No. 6,492,314, the contents of which are incorporated herein by reference.

Regardless of the type of cleaning product, it may additionally include conventional ingredients, adjuvants such as various coloring agents and perfumes; ultraviolet light absorbers, salts such as sodium chloride or magnesium sulfate heptahydrate; hydrotropes such as sodium cumene sulfonate or preferably sodium xylene sulfonate; chelators or sequestering agents, e.g., EDTA, HEDTA, or preferably pentasodium DTPA; pH modifiers, e.g., sodium hydroxide or sulfuric acid; etc., preservatives, such as sodium formate, formalin, or 1,3-dimethylol-5,5-dimethyl-hydantoin (DMDM hydantoin), color stabilizers such as sodium bisulfite, and anti-mycotic or antibacterial agents, such as triclosan.

For example, the invention provides a dishwashing liquid comprising, by weight:

(i) about 5% to about 45% of combined magnesium and sodium salts of a $C_8$-$C_{18}$ linear alkyl sulfonate surfactant, where the sodium salt can vary between about 0% and about 20%, preferably between 3% and 15% and the magnesium salt can vary between about 0% and about 35%, preferably about 3% and about 15%;
(ii) about 1% to about 10% of a $C_{12}$/$C_{14}$ alkyl amido propyl dimethyl amine oxide surfactant;
(iii) 0.35% to 3 wt. % of a fragrance component comprising the malodor reducing fragrance of the invention;
(iv) 5% to 35% of a $C_8$-$C_{18}$ ethoxylated alkyl ether sulfate;
(v) 0% to 10% ethanol;
(vi) 1% to 5% sodium xylene sulfonate;
(vii) 0% to 1% pentasodium pentatate;
(viii) 0% to 0.5% 1,3-dimethylol-5,5-dimethyl-hydantoin; and
(ix) water.

The total of components of the dishwashing liquid other than water and fragrance (sometime referred to as the Active Ingredient or AI fraction) in the dishwashing liquids of the invention is about 25-40%, e.g., about 30 to 36%. For example, in one preferred embodiment, the AI fraction is about 36% and the fragrance level is about 0.9%. The dishwashing liquid may be conveniently provided in a plastic squeeze bottle with a small orifice in the cap to permit the liquid to be dispensed. The optimal diameter of the orifice may vary depending on the viscosity and other properties of the dishwashing liquid, but is typically 3-5 mm, for example 3.4 or 4.2 mm.

The compositions and products of the invention may be readily prepared by conventional means using, e.g., simple mixing methods.

The invention also includes methods of reducing and/or eliminating malodor in a cleaning or dishwashing implement by application of the fragrance composition or a cleaning product of the invention to the implement. The implement may include any used in the cleaning or washing of tools, devices, surfaces, or containers used in the preparation or disposal of food. For example, rags, sponges, trays, abrasive pads, scrubbies, poufs, wipes, brushes, trash receptacles or cans, liners for such receptacles, food storage containers, are included.

The invention includes methods off reducing and/or eliminating malodor in a space by the agitation of the fragrance composition or a cleaning product of the invention in water. Spaces in which the invention can be used to eliminate or reduce malodor include any in which food is consumed, disposed of, stored, or prepared. Specifically, such places include kitchens, dining rooms, restaurants, trash storage rooms, and dishwashing rooms, refrigerators, freezers, storerooms, and trash dumpsters. By agitation, it is meant any activities that disrupt the water into which the composition has been placed, thereby resulting in the volatilization of some of the components in the compositions. Agitation includes dishwashing (manual or automatic), handwashing or machine washing of textiles, the motions carried out when washing one's hands, mopping or wiping of floors and surfaces, and spraying.

EXAMPLES

Example 1

A fragrance composition 1 is prepared by admixing the following ingredients:

| Composition 1 | |
|---|---|
| Ingredient | % by weight |
| Aldehyde C10 | 2.50 |
| Allyl Amyl Glycolate | 1.00 |
| Cis-3-hexenyl acetate | 1.00 |
| Rose Oxide | 0.50 |
| Terpinolene | 2.00 |
| Zestover | 3.00 |
| Orange terpenes | 40.00 |
| Isononyl acetate | 5.00 |
| Dorisyl ®[(1)] | 10.00 |
| Terpinyl acetate | 10.00 |
| Dihydromyrcenol | 15.00 |
| Citronellyl nitrile | 10.00 |
| Total | 100.00 |

[(1)]p-tert-butyl-cyclohexyl acetate; available from Firmenich SA, Geneva, Switzerland Likewise, a comparative fragrance A, is prepared as follows:

| Fragrance A | |
|---|---|
| Ingredient | % by weight |
| Dipropylene glycol | 10.00 |
| Orange terpenes | 40.00 |
| Isononyl acetate | 5.00 |
| Dorisyl ®[(1)] | 10.00 |
| Terpinyl acetate | 10.00 |
| Dihydromyrcenol | 15.00 |
| Citronellyl nitrile | 10.00 |
| Total | 100.00 |

[(1)]p-tert-butyl-cyclohexyl acetate; origin: Firmenich SA, Geneva, Switzerland

Various samples of these two compositions are then incorporated in a dishwashing product having the composition of Example 2 hereof, in the concentration indicated below, and tested for their efficiency in reducing typical cooking and residual food malodors.

Example 2

Dishwashing Liquid

A dishwashing liquid for use in combination with the fragrance components of examples 1 is prepared by combining the following ingredients:

| Ingredients | Formula % by weight |
|---|---|
| NaLAS | 3.71 |
| MgLAS | 11.16 |
| NH4 AEOS-1.3EO | 14.23 |
| Amine Oxide | 6.70 |
| SXS | 3.30 |
| Sodium Bisulfite | 0.10 |
| Salt | 0.22 |
| Ethanol | 5.25 |
| Sequestering agent | 0.28 |
| Preservative | 0.11 |
| Fragrance Component of Ex. 1 or 2 | 0.60 |
| Water and minors (color, pH adjustment) | BALANCE |

In the table above:

NaLAS and Mg LAS refer to the sodium and magnesium salts resp. of linear $C_{12}$-$_{14}$ alkyl benzene sulfonates.

NH4AEOS-1.3EO refers to $C_8$-$C_{18}$ alcohol ethoxylate compounds with an average of 1.3 ethoxy groups.

Amine oxide refers to $C_{12}$-$_{14}$ alkylamido propyl dimethyl amine oxide.

SXS refers to sodium xylene sulfonate.

We claim:

1. A fragrance composition comprising:

a. a decyl aldehyde;

b. an allyl amyl glycolate;

c. cis-3-hexenyl acetate;

d. a rose oxide;

e. a terpinolene; and f. 2,4-dimethyl-3-cyclohexene-1-carbaldehyde.

2. The composition of claim 1, further comprising one or more of:

a. an amyl cinnamic aldehyde in an amount of less than about 15%, b. 1,3,4,6,7,8-hexahydro-4,6,6,7,8,8-hexamethylcyclopenta-g-2-benzopyran in an amount of less than about 20%, c. 1-(1,2,3,4,5,6,7,8-octahydro-2,3,8,8-tetramethyl-2-naphthalenyl)ethanone, in an amount of less than 5%.

3. The composition of claim 1, wherein the decyl aldehyde is present in an amount of about 0.5 to about 5%.

4. The composition of claim 1, wherein allyl amyl glycolate is present in an amount of about 0.5 to about 5%.

5. The composition of claim 1, wherein the cis-3-hexenyl acetate is present in an amount of about 0.1 to about 3%.

6. The composition of claim 1, wherein the rose oxide is present in an amount of about 0.01 to about 0.5%.

7. The composition of claim 1, wherein the terpinolene is present in amount of about 0.05 to about 7%.

8. The composition of claim 1, wherein the 2,4-dimethyl-3-cyclohexene-1carbaldehyde is present in an amount of about 0.05 to about 2%.

9. The composition of claim 1, wherein the composition comprises one or more of:

a. amyl cinnamic aldehyde in an amount of less than about 5%, b. 1,3,4,6,7,8-hexahydro-4,6,6,7,8,8-hexamethylcyclopenta-g-2-benzopyran in an amount of less than about 5%, and c. 1-(1,2,3,4,5,6,7,8-octahydro-2,3,8,8-tetramethyl-2-naphthalenyl)ethanone in an amount of less than about 2%.

10. The composition of claim 1 further comprising an ingredient selected from an orange terpene; an acetate of a $C_{6-12}$ alcohol; a $C_{10}$ unsaturated alcohol; and citronellyl nitrile.

11. The composition of claim 1 further comprising a surfactant.

12. The composition of claim 11, wherein surfactant is selected from a nonionic surfactant and a mixture of ionic surfactants and nonionic surfactants.

13. The composition of claim 11, wherein the surfactant comprises at least one surfactant selected from the group consisting of a cationic surfactant, a nonionic surfactant, $C_8$-$C_{18}$ linear alkyl benzene sulfonate salt, sulfated alcohol ethoxylates, amine oxide surfactants and amphoteric surfactants.

14. The composition of claim 11, wherein the surfactant comprises, by weight,:

a. about 5% to about 45% of salts of a $C_8$-$C_{18}$ linear alkyl sulfonate surfactant;

b. about 1% to about 10% of a $C_{12}$/$C_{14}$ alkyl amido propyl dimethyl amine oxide surfactant; and c. about 5% to about 35% of a $C_8$-$C_{18}$ ethoxylated alkyl ether sulfate.

15. The composition of claim 14, wherein the salt of a $C_8$-$C_{18}$ linear alkyl sulfonate surfactant is selected from a sodium salt, a magnesium salt, and mixtures thereof.

16. The composition of claim 11, wherein the surfactant comprises up to about 10 weight % of a $C_{12}$/$C_{14}$ alkyl amido propyl dimethyl amine oxide surfactant and about 5% to about 35% of a $C_8$-$C_{18}$ ethoxylated alkyl ether sulfate.

17. The composition of claim 16 further comprising at least one of the following:

a. up to about 10% ethanol;

b. up to about 5% sodium xylene sulfonate;

c. up to about 1% pentasodium pentatate; and d. up to about 0.5% 1,3-dimethylol-5,5-dimethyl-hydantoin.

18. The composition of claim 1 comprising:

a. 0.5 to 5% by weight of the decyl aldehyde;

b. 0.5 to 5% by weight of the allyl amyl glycolate;

c. 0.1 to 3% by weight of the cis-3-hexenyl acetate;

d. 0.01 to 0.5% by weight of the rose oxide;

e. 0.05 to 7% by weight of the terpinolene; and f. 0.05 to 2% by weight of the 2,4-dimethyl-3-cyclohexene-1-carbaldehyde.

19. The composition of claim 1 comprising a. about 2.5% by weight of the decyl aldehyde;

b. about 1% by weight of the allyl amyl glycolate;

c. about 1% by weight of the cis-3-hexenyl acetate;

d. about 0.5% by weight of the rose oxide;

e. about 2% by weight of the terpinolene; and f. about 3% by weight of the 2,4-dimethyl-3-cyclohexene-1-carbaldehyde.

20. The composition of claim 1 comprising a. about 0.5% by weight of the decyl aldehyde;

b. about 1.5% by weight of the allyl amyl glycolate;

c. about 0.1% by weight of the cis-3-hexenyl acetate;

d. about 0.1% by weight of the rose oxide;

e. about 1% by weight of the terpinolene; and f. about 0.5% by weight of the 2,4-dimethyl-3-cyclohexene-1-carbaldehyde.

* * * * *